(12) United States Patent  (10) Patent No.: US 8,241,575 B2
Murray et al.                   (45) Date of Patent:       Aug. 14, 2012

(54) MOLECULARLY IMPRINTED POLYMER SENSOR DEVICE

(75) Inventors: George M. Murray, Tullahoma, TN (US); Andrew F. Mason, Silver Spring, MD (US); Edward W. Ott, Jr., Dundalk, MD (US)

(73) Assignee: The Johns Hopkins University, Baltimore, MD (US)

( * ) Notice: Subject to any disclaimer, the term of this patent is extended or adjusted under 35 U.S.C. 154(b) by 605 days.

(21) Appl. No.: 12/360,372

(22) Filed: Jan. 27, 2009

(65) Prior Publication Data

US 2009/0197297 A1   Aug. 6, 2009

Related U.S. Application Data

(60) Provisional application No. 61/023,901, filed on Jan. 28, 2008.

(51) Int. Cl.
*G01N 15/06* (2006.01)
*G01N 33/00* (2006.01)
*G01N 33/48* (2006.01)

(52) U.S. Cl. ........... 422/82.07; 422/50; 422/52; 422/53; 422/401; 422/402; 422/405; 422/68.1; 422/82.05; 422/82.06; 422/82.08; 422/82.09; 436/43; 436/164

(58) Field of Classification Search ............ 422/50, 422/52, 53, 400, 401, 402, 405, 68.1, 82.05, 422/82.06, 82.07, 82.08, 82.09; 436/43, 436/164
See application file for complete search history.

(56) References Cited

U.S. PATENT DOCUMENTS

| | | | |
|---|---|---|---|
| 5,312,940 A | 5/1994 | Grubbs et al. | |
| 5,342,909 A | 8/1994 | Grubbs et al. | |
| 5,831,108 A | 11/1998 | Grubbs et al. | |
| 5,917,071 A | 6/1999 | Grubbs et al. | |
| 5,969,170 A | 10/1999 | Grubbs et al. | |
| 5,977,393 A | 11/1999 | Grubbs et al. | |
| 6,020,207 A * | 2/2000 | Liu | 436/164 |
| 6,111,121 A | 8/2000 | Grubbs et al. | |
| 6,153,147 A * | 11/2000 | Craig | 422/408 |
| 6,211,391 B1 | 4/2001 | Grubbs et al. | |
| 6,225,488 B1 | 5/2001 | Mukerjee et al. | |
| 6,557,484 B1 * | 5/2003 | Engelman | 116/206 |
| 6,593,142 B2 | 7/2003 | Kelly et al. | |
| 6,924,147 B2 | 8/2005 | Kelly et al. | |

(Continued)

FOREIGN PATENT DOCUMENTS

WO    98/39346    9/1998

(Continued)

*Primary Examiner* — Brian J Sines
(74) *Attorney, Agent, or Firm* — Noah J. Hayward

(57) ABSTRACT

A molecularly imprinted polymer sensor device for detecting the presence of a taggant molecular structure in a fluid is disclosed. The molecularly imprinted polymer sensor device comprises a molecularly imprinted crosslinked polymer having a crosslinked core and a plurality of polymer arms attached to the core, wherein the core has molecular sized cavities adapted to selectively receive and bind displacement molecules having the taggant molecular structure and a colorimetric indicator, said displacement molecule being selectively removed from the molecularly imprinted crosslinked polymer and replaced with the taggant molecular structure upon exposure to the fluid containing the taggant molecular structure therein, thereby indicating the presence of the taggant molecular structure in the fluid.

12 Claims, 3 Drawing Sheets

U.S. PATENT DOCUMENTS

| | | |
|---|---|---|
| 7,238,533 B1 * | 7/2007 | Legge et al. ............ 436/166 |
| 7,288,415 B2 | 10/2007 | Huang |
| 7,319,038 B2 | 1/2008 | Southard et al. |
| 7,799,568 B2 * | 9/2010 | Charles et al. ............ 436/56 |
| 2007/0128423 A1 | 6/2007 | Belfort et al. |

FOREIGN PATENT DOCUMENTS

| | | |
|---|---|---|
| WO | 99/00396 | 1/1999 |
| WO | 99/00397 | 1/1999 |
| WO | 99/28330 | 6/1999 |
| WO | 99/29701 | 6/1999 |
| WO | 99/50330 | 10/1999 |
| WO | 99/51344 | 10/1999 |
| WO | 00/15339 | 3/2000 |
| WO | 00/58322 | 10/2000 |
| WO | 00/71554 | 11/2000 |

* cited by examiner

GHB TAGGED WITH
METHYLENE BLUE

KETAMINE TAGGED WITH
METHYLENE BLUE

CORTISOL TAGGED WITH
METHYLENE BLUE

MOLECULARLY IMPRINTED POLYMER SENSOR DEVICE

CROSS-REFERENCE TO RELATED APPLICATIONS

This application claims the benefit of prior filed U.S. Provisional Application No. 61/023,901, filed Jan. 28, 2008, the contents of which are incorporated by reference herein.

BACKGROUND OF THE INVENTION

1. Field of the Invention

The present invention generally relates to a molecularly imprinted polymer sensor device for measuring and detecting a wide variety of target molecules in a fluid.

2. Description of the Related Art

In the technical field of chemistry and particularly analytical chemistry there are varied means for analyzing fluids of varied types to determine particular chemical content. Among the more common systems are liquid samplers, multi-compartment test kits (e.g., such as those used for testing pH and chlorine content in swimming pools), dye indicators kits and reagent strips. Currently analytical liquid samplers and test strips are used in areas that include the fields of medicine, drug detection, water quality, industrial pollutants and generally in the environmental arena.

There has become an urgent need to test all types of beverages for different substances. There has been an increased incidence in the use of drugs which overpower individuals to enable the drug supplier to commit a criminal act such as sexual assault. The top five drugs used in drug facilitated sexual assault are Rohypnol, ketamine, gamma-hydroxybutyrate (GHB), gamma butyrolactone (GBL), and 1,4-butanediol.

Rohypnol, also known as flunitrazepam, has the chemical formula 5-(2-fluorophenyl)-1,3,dihydro-1 methyl-7 nitro-2H-1,4-benzodiazepin-2-one. Rohypnol has been known to be in use as a date rape drug since the early 1990s. The hypnotic effects of Rohypnol predominate over its sedative effects, and Rohypnol is ten times as potent as Valium.

Ketamine, a cousin of PCP, was introduced in the 1960s as an anesthetic and is now used commonly be veterinarians when performing surgeries. The chemical formula of Ketamine is $C_{13}H_{16}ClNO$. It is also produced under the brand names of Ketajet, Ketaset, and Ketelar.

GHB, which has the chemical formula $C_4H_8O_3$, is a naturally occurring metabolite of GABA, which is thought to function as a neurotransmitter. GHB has been used to enhance muscle strength and increase the release of growth hormone. It has also been used as a CNS (central nervous system) depressant. GHB has several chemical precursors, two of which are GBL and 1,4-butanediol.

GBL is a commercially available solvent found in most floor strippers and pine needle oil. When ingested, it is converted to GHB.

These substances, collectively known as date rape drugs, were not originally intended for the purposes that now seem prevalent. All of these substances have been or still are used for legitimate and productive purposes. Rohypnol has been used to treat severe sleep disorders. Ketamine was used during the Vietnam War as an anesthetic and pain reliever and is still in use today. GHB has also been used for sleep disorders as well as to enhance muscle strength. GBL and 1,4-butanediol, though not manufactured for use in the human body, have been used in the production of plastics, textiles, and cleaning supplies.

These date rape drugs, which can act in as little as 20 minutes and have effects lasting up to 12 hours, have been increasing in use. Drug rape usually goes unchecked since the victims are unable to remember the events or details and therefore are unreliable witnesses in any legal action. Even if the victim can remember some details or have suspicions they are often unwilling to come forward.

One common method date rape perpetrators use to drug a victim is by putting a date rape drug into the victim's drink unbeknownst to the victim. Some perpetrators are able to introduce a drug into a drink quickly and without the appearance of wrongdoing. These factors have made it increasingly more dangerous to consume beverages in social settings such as bars and restaurants, or even as a guest in someone's residence. As the public has become more aware of drug facilitated sexual assaults, there has become an increased need for a product that can help prevent these victimizations.

Accordingly, it would be desirable to provide a testing means which will enable users to test, for example, their beverage to establish whether it is safe to drink. The benefits of a testing method include that the user knows that the beverage is safe to drink. A further benefit of a testing method is that where the presence of a drug is detected, there is a possibility that the perpetrator may be identified. Any such device could also be used by authorities to screen drinks at the scene of an alleged offense.

SUMMARY OF THE INVENTION

In accordance with one embodiment of the present invention, a molecularly imprinted polymer sensor device for detecting the presence of a taggant molecular structure in a fluid is provided comprising a molecularly imprinted crosslinked polymer having a crosslinked core and a plurality of polymer arms attached to the core, wherein the core has molecular sized cavities adapted to selectively receive and bind displacement molecules having the taggant molecular structure and a colorimetric indicator, said displacement molecules being selectively removed from the molecularly imprinted crosslinked polymer upon exposure to the fluid containing the taggant molecular structure therein, thereby indicating the presence of the specific taggant molecular structure in the fluid.

In accordance with a second embodiment of the present invention, an apparatus for detecting the presence of a specific taggant molecular structure in a fluid is provided comprising a housing having an inlet to receive a flow of the fluid, wherein the inlet is coated with a molecularly imprinted crosslinked polymer having a crosslinked core and a plurality of polymer arms attached to the core, wherein the core has molecular sized cavities adapted to selectively receive and bind displacement molecules having the taggant molecular structure and a calorimetric indicator, said displacement molecules being selectively removed from the molecularly imprinted crosslinked polymer upon exposure to the fluid containing the taggant molecular structure therein, thereby indicating the presence of the specific taggant molecular structure.

In accordance with a third embodiment of the present invention, a method for detecting the presence of a taggant molecular structure in a fluid is provided comprising (a) providing a molecularly imprinted polymer sensor device for detecting the presence of a taggant molecular structure in a fluid comprising a molecularly imprinted crosslinked polymer having a crosslinked core and a plurality of polymer arms attached to the core, wherein the core has molecular sized cavities adapted to selectively receive and bind displacement molecules having the taggant molecular structure and a calorimetric indicator; (b) contacting the molecularly imprinted crosslinked star polymer with the fluid, wherein said displacement molecules are selectively removed from the molecularly imprinted crosslinked polymer upon exposure to the taggant molecular structure in the fluid thereby indicating the presence of the taggant molecular structure in the fluid; and (c) correlating a color change in the fluid with the amount of the taggant molecular structure in the fluid.

Applicants have come to appreciate, for many taggant detecting applications, the development of small, portable sensor devices which are relatively highly-selective and sensitive to a specific taggant molecular structure, and are capable of detecting the specific taggant molecular structure in a convenient and expeditious manner, is of particular interest.

BRIEF DESCRIPTION OF THE DRAWINGS

Various embodiments are described below with reference to the drawings wherein.

DETAILED DESCRIPTION OF PREFERRED EMBODIMENT(S)

Figure 1:
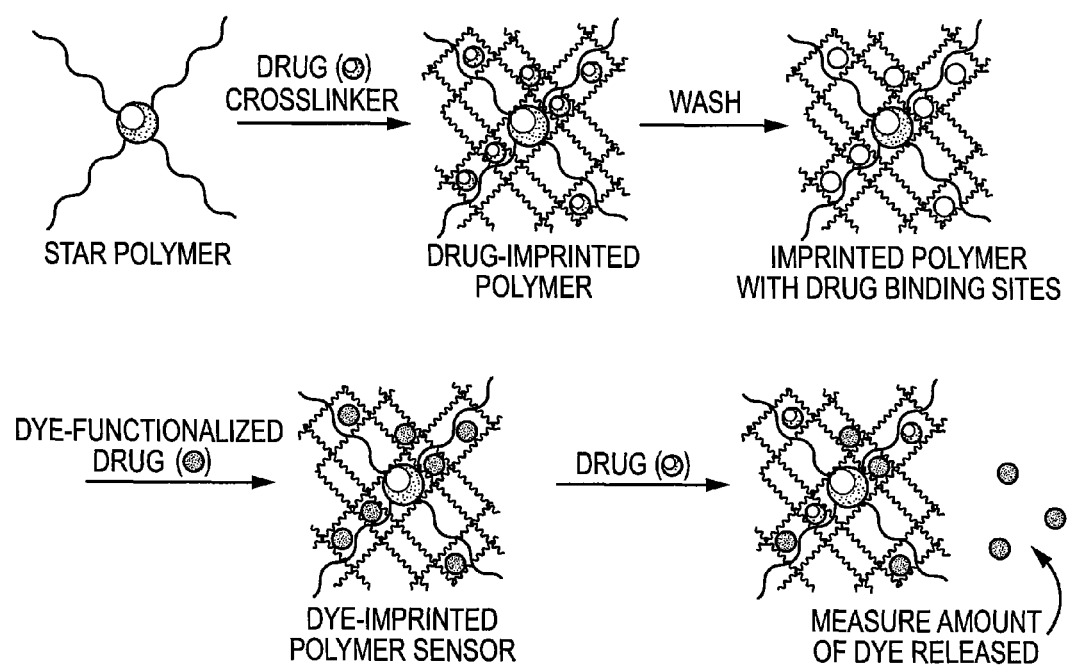
FIG. 1 illustrates a reaction scheme for preparing a molecularly imprinted crosslinked polymer according to one embodiment of the present invention

The present invention is directed to a sensor device that employs a molecularly imprinted polymer a crosslinked core and a plurality of polymer arms attached to the core, wherein the core has molecular sized cavities adapted to selectively receive and bind displacement molecules having the taggant molecular structure and a calorimetric indicator. The present invention uses the techniques of molecularly imprinting polymer devices for providing selective binding sites for receiving displacement molecules having a taggant molecular structure and a calorimetric indicator in order to detect the presence of a specific taggant molecular structure such as a hormone, a drug, or a drug residue in a fluid. In one embodiment, the sensor device is used to detect the presence of a specific taggant molecular structure in fluids, and particularly to varied beverages ingested by humans such as, for example, soda, fruit juices, alcoholic punches, cocktails, beer, tonic water and the like. For example, in this embodiment, the sensor device is particularly suited for analyzing beverages that can contain a drug such as gamma hydroxybutyric acid, flunitrazepam (ROHYPNOL), ketamine, gamma-hydroxybutyrate (GHB), gamma butyrolactone (GBL) and the like. In another embodiment, the sensor device is used to detect the presence of a specific taggant molecular structure such as a hormone, e.g., cortisol or hydrocortisol, in a biological fluid such as blood, saliva and the like. For example, cortisol (or hydrocortisone) is a corticosteroid hormone involved in the body's response to stress. Accordingly, the sensor device can determine the level of stress in a subject by indicating the presence of cortisol in the biological fluid.

The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer, either covalently or by other interactions such as ionic, hydrophobic or hydrogen bonding, so that recognition sites for the template molecule can be provided in the substrate material. The template molecule is then removed from the substrate to leave a "cavity" or recognition site. Pauling reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

The target or template molecule directs the positioning of the encapsulating antibody by the interactions that occur between certain sites on the target and complementary sites on the antibody. The sites that allow complementary associations are certain arrangements of atoms that exhibit an electrostatic attraction of a specific kind. These localized atomic arrangements are sometimes referred to as "functional groups." The functional groups on a molecule help to define the molecule's overall chemical properties. In general, the MIP should exhibit as closely as possible the reverse topology of the template molecule.

The soluble, processable molecularly imprinted crosslinked polymers (MIPs) are made by first building a core with a plurality of arms attached to the core. The core is usually dissolved in a larger amount of other polymerizable molecules. The bulk of the other molecules of the polymer are made with crosslinking monomers and specific target compounds. These molecules have two places to bind to the polymer chain to form a rigid three-dimensional structure. The crosslinkers are necessary to hold the displacement molecules having the taggant molecular structure and colorimetric indicator after the target molecule (also called a "template", "analyte" or "taggant") is removed.

It is worthy to note, that while specific target compounds are used to form the soluble, processable molecularly imprinted crosslinked polymers, the polymers may have a high affinity for a class of compounds that is substantially similar to the target compound. A molecularly imprinted polymer may bind a number of compounds that are similar in shape, charge density, geometry or other physical or chemical properties.

As used herein, the term "bind," "binding," "bond," "bonded," or "bonding" refers to the physical phenomenon of chemical species being held together by attraction of atoms to each other through sharing, as well as exchanging, of electrons or protons. This term includes bond types such as: ionic, coordinate, hydrogen bonds, covalent, polar covalent, or coordinate covalent. Other terms used for bonds such as banana bonds, aromatic bonds, or metallic bonds are also included within the meaning of this term.

As used herein, "reaction" is intended to cover single step and multi-step reactions which can be direct reactions of reactants to products or may include one or more intermediate species which can be stable or transient.

Representative examples of target compounds contemplated according to the present invention include, but are not limited to, a hormone, a drug, a drug residue and the like. Examples of a hormone include cortisol, hydrocortisone and the like. Examples of drugs include gamma hydroxybutyric acid, flunitrazepam (ROHYPNOL), ketamine, gamma-hydroxybutyrate (GHB), gamma butyrolactone (GBL) and the like.

The soluble, processable molecularly imprinted crosslinked polymers can be prepared by any technique known in the art. In one embodiment, the molecularly imprinted crosslinked polymer is prepared using techniques of controlled radical polymerization, i.e. by atom-transfer radical polymerization (ATRP) or reversible addition-fragmentation chain transfer (RAFT) polymerization. The RAFT technique for producing structured polymers is known from the prior art. RAFT polymerization employs a chain transfer agent that allows construction of the MIP with a well-defined molecular weight distribution and incorporates functional groups at the end of the linear polymer arms. RAFT polymerization is particularly preferred because it is compatible with a wide variety of vinyl monomers. In this embodiment, a molecularly imprinted crosslinked polymer is grown from a central core molecule that incorporates a RAFT agent having functional groups.

Examples of RAFT agents include dithiocarbamates, aliphatic or aromatic dithioesters and the like. In one embodiment, a three armed Raft agent is prepared as shown in Scheme I below.

SCHEME I

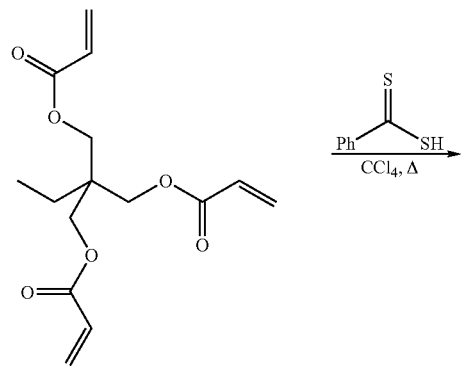

In another embodiment, a four armed trithiocarbonate RAFT agent is prepared as shown in Scheme II below.

SCHEME II

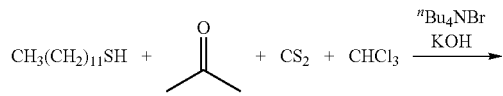

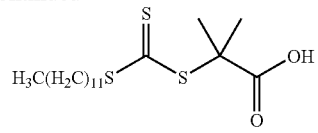

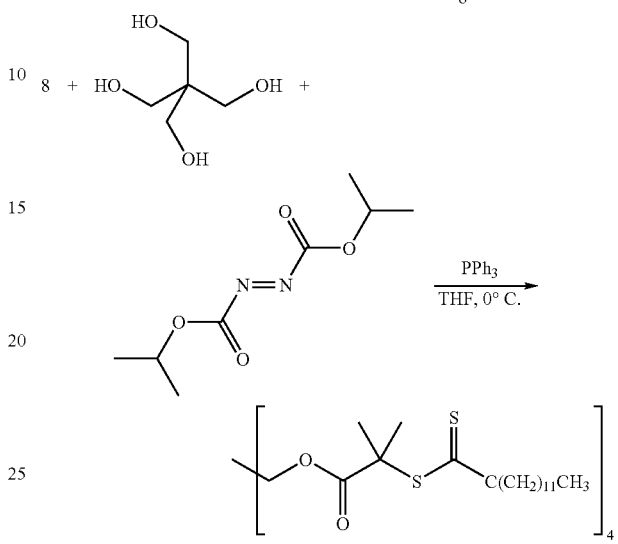

In general, the molecularly imprinted crosslinked polymer is first prepared by forming a core having linear polymer arms attached thereto employing a RAFT agent under polymerization conditions known in the art. For example, the core is formed by subjecting a mixture containing at least a functional monomer, RAFT agent and photoinitiator to a source of ultraviolet radiation and/or elevated temperature, e.g., above about 50° C., and curing the mixture. A wide variety of functional monomers may be used for synthesizing the molecularly imprinted crosslinked polymer in accordance with the principles of the present invention. Suitable non-limiting examples of functional monomers include $C_1$-$C_{20}$ alkyl and $C_3$-$C_{20}$ cycloalkyl (meth)acrylates such as methyl methacrylate, substituted and unsubstituted $C_6$-$C_{30}$ aryl (meth)acrylates, allyl acrylates and methacrylates, cyanoacrylate, acrylamides such as N,N-dimethylacrylamide and N,N-dimethylmethacrylamide, styrene, methyl styrene, 4-butenyl styrene, and the like and mixtures thereof. Typically, at least about 50 equivalents of functional monomer are reacted for every core molecule.

Typical polymerization initiators include free-radical-generating polymerization initiators such as acetyl peroxide, lauroyl peroxide, decanoyl peroxide, caprylyl peroxide, benzoyl peroxide, tertiary butyl peroxypivalate, sodium percarbonate, tertiary butyl peroctoate, and azobis-isobutyronitrile (AIBN). The curing process will of course depend upon the initiator used and the physical characteristics of the monomer or monomer mixture such as viscosity. In any event, the level of initiator employed will vary within the range of about 0.001 to about 2 weight percent of the mixture of monomers.

Polymerization to form the resulting core can be carried out in the presence or absence of a solvent. Suitable solvents are in principle a solvent is capable of dissolving all of the monomers present in the monomer mixture. Suitable solvent include aliphatic or aromatic hydrocarbon solvent such as toluene, xylene and the like, halogenated hydrocarbon solvents such as methylene chloride, and the like. In one embodiment, the core can be prepared as set forth below in Scheme IV:

SCHEME III

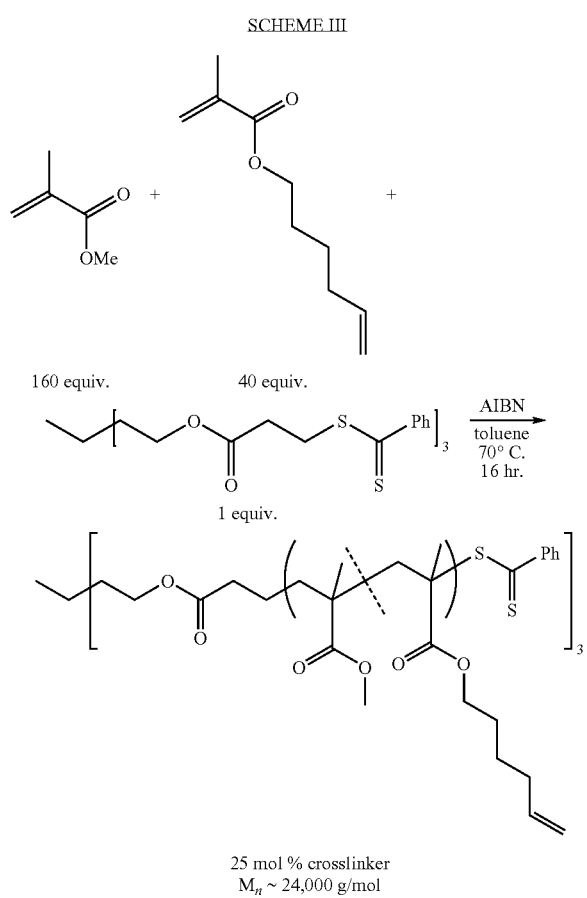

25 mol % crosslinker
$M_n \sim 24{,}000$ g/mol

The amount and type of polymer arms needed for a given molecularly imprinted crosslinked polymer will depend on the number of coordination sites available on the target compound and the associated arms. For example, a molecularly imprinted crosslinked polymer may contain a target compound with 4 coordination sites. The polymers arms can be random copolymer arms, block copolymer arms and the like. In addition, the resulting polymer arms attached to the core should allow for the molecularly imprinted crosslinked polymer to be a soluble, processable material, i.e., make the resulting molecularly imprinted crosslinked polymer soluble in, e.g., organic solvents to facilitate their application (coating) to surfaces. In this manner, the molecularly imprinted crosslinked polymer is capable of being dissolved or coated onto a surface of an apparatus in order to detect the target molecule as discussed hereinbelow.

Once the core is formed, the core is then reacted with a crosslinking agent to form the soluble, processable molecularly imprinted crosslinked polymer having the imprinted binding sites. Crosslinking agents that impart rigidity or structural integrity to the molecularly imprinted crosslinked polymer are known to those skilled in the art. The molecularly imprinted crosslinked polymer must have sufficient rigidity so that the target molecule may be easily removed without affecting the integrity of the polymer. Examples of such crosslinking agents include, but are not limited to, di- tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanatoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoxaspiro[5,5]undecane; divinyl tin dichloride and the like. In one embodiment, a crosslinking agent can be an acrylamide-containing monomer prepared as generally set forth below in Scheme IV:

SCHEME IV

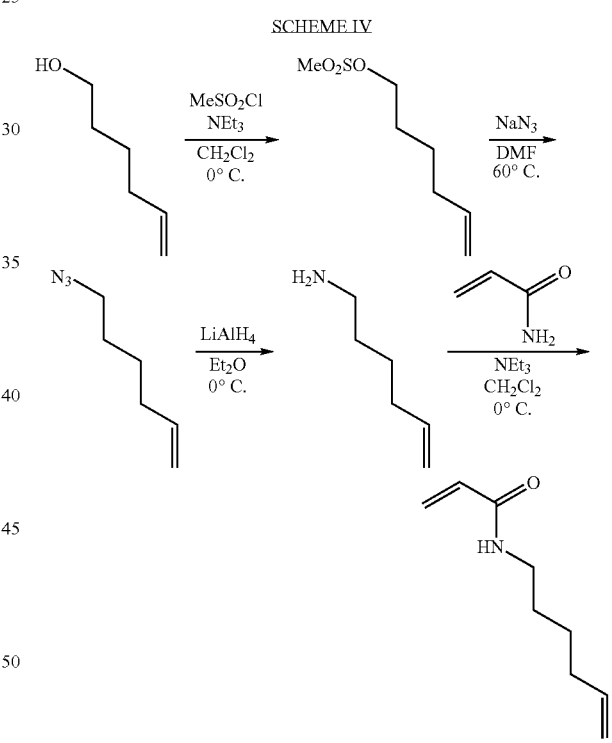

The choice of crosslinking agent will be dictated by the chemical (hydrophilicity, chemical stability, degree of crosslinking, ability to graft to other surfaces, interactions with other molecules, etc.) and physical (porosity, morphology, mechanical stability, etc.) properties desired for the polymer. The amounts of the core having linear arms attached thereto and crosslinking agent should be chosen to provide a crosslinked polymer exhibiting the desired structural integrity and hydrophilicity. The amounts can vary broadly, depending on the specific nature/reactivities of the core, monomer and crosslinking agent chosen as well as the specific application and environment in which the polymer will ultimately be employed. The relative amounts of each reactant can be varied to achieve desired concentrations of complexes in the polymer support structure. The degree of crosslinking may, however, affect the amount of flux, i.e., a lower degree of crosslinking may provide a higher flux. The degree of crosslinking herein can range from about 5% to about 95%.

The molecularly imprinted crosslinked polymer according to the present invention is prepared by an olefin metathesis crosslinking reaction of the core, crosslinker and a Grubbs catalyst as is well known in the art. As an initial matter, "olefin metathesis," as it is understood in the art, refers to the metal-catalyzed redistribution of carbon-carbon bonds in a reaction involving an olefin. While the invention is broadly applicable to almost all reactions involving olefin metathesis catalysts, some of these catalysts are better known than others. For example, over two decades of intensive research effort has culminated in the discovery of well-defined ruthenium and osmium carbenes, useful in the invention, that are highly active olefin metathesis catalysts and stable in the presence of a variety of functional groups. Among the catalysts of interest are the neutral ruthenium or osmium metal carbene complexes that possesses metal centers that are formally in the +2 oxidation state, have an electron count of 16, and are penta-coordinated. Other catalysts of particular interest include, but are not limited to, cationic ruthenium or osmium metal carbene complexes that possesses metal centers that are formally in the +2 oxidation state, have an electron count of 14, and are tetra-coordinated. Examples of such metathesis catalysts have been previously described in, for example, U.S. Pat. Nos. 5,312,940; 5,342,909; 5,831,108; 5,969,170; 6,111,121; 6,211,391; 5,917,071; 5,977,393; and 6,225,488 and PCT Publications WO 98/39346, WO 99/00396, WO 99/00397, WO 99/28330, WO 99/29701, WO 99/50330, WO 99/51344, WO 00/15339, WO 00/58322 and WO 00/71554, the disclosures of each of which are incorporated herein by reference to the extent relevant. The ruthenium and osmium carbene complexes disclosed in these patents all possess metal centers that are formally in the +2 oxidation state, have an electron count of 16, and are penta-coordinated. A preferred Grubbs catalyst for use herein is a second generation Grubbs catalyst.

Generally, the target molecule is added incorporated into the molecularly imprinted crosslinked polymer during the crosslinking reaction. For example, in the case of cortisol, a cortisol solution of methylene chloride is added to the mixture and will associate with the molecularly imprinted crosslinked polymer through hydrogen bonding interactions with the amide functional groups, forming imprint sites with the polymer matrix. When polymerization is complete, the target molecule is removed from the molecularly imprinted crosslinked polymer and replaced by the displacement molecule. See, e.g., FIG. 1. Removal of the target molecule leaves a molecularly imprinted crosslinked polymer having complementary molecular cavities that have specific binding affinity for the target molecule. The target molecule comprising, for example, a hormone or drug as discussed above, may be dissociated from the binding site within the polymer in a manner that does not adversely affect the imprinted cavity. In embodiments wherein the target molecule is covalently bound to the functional monomer, any appropriate method can be used to cleave the covalent bond, although the covalent bond formed should preferably be cleaved under conditions suitable to release the imprint molecule after the molecularly imprinted crosslinked polymer is formed, without adversely affecting the selective binding characteristics of the molecularly imprinted crosslinked polymer. To accomplish this, acetone, isopropanol, methanol or other suitable organic solvent may be used. In embodiments wherein the target molecule is associated with the complex in a non-covalent manner, the non-covalently bound molecule is simply leached or washed out after polymerization.

Figure 2:
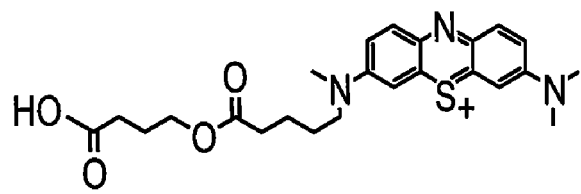
FIG. 2 depicts the structural representation of exemplary displacement molecules for use in the molecularly imprinted crosslinked polymer of the present invention.
Figure 2:
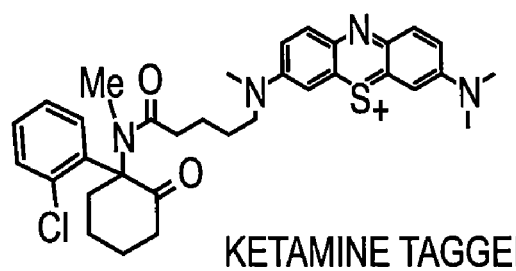
Figure 2:
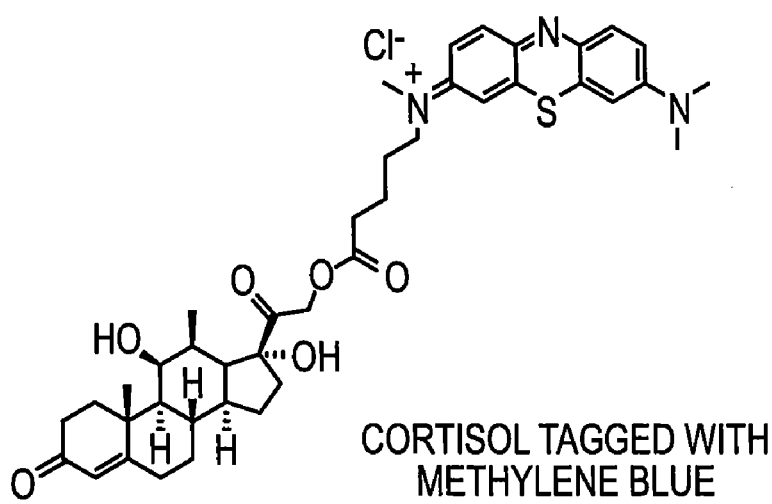

Next, displacement molecules having the taggant molecular structure and calorimetric indicator are introduced into the vacant binding sites. Displacement molecules for use herein will have the taggant molecular structure to be detected in the fluid and a colorimetric indicator which will indicate that the target molecule is in the fluid, as discussed hereinbelow. In a preferred embodiment, a calorimetric indicator is methylene blue. However, any number of alternative dye molecules can be used such as, for example, Auramine O, Azure A, Azure B, Basic Fuchsin, Crystal Violet, Darrow Red, Ethyl Eosin, Nile Blue and the like. Representative examples of suitable displacement molecules are shown in FIG. 2. Methods for preparing the displacement molecules are within the purview of one skilled in the art and exemplified in the examples. Specific examples of preparing a displacement molecule is generally depicted below in Scheme V.

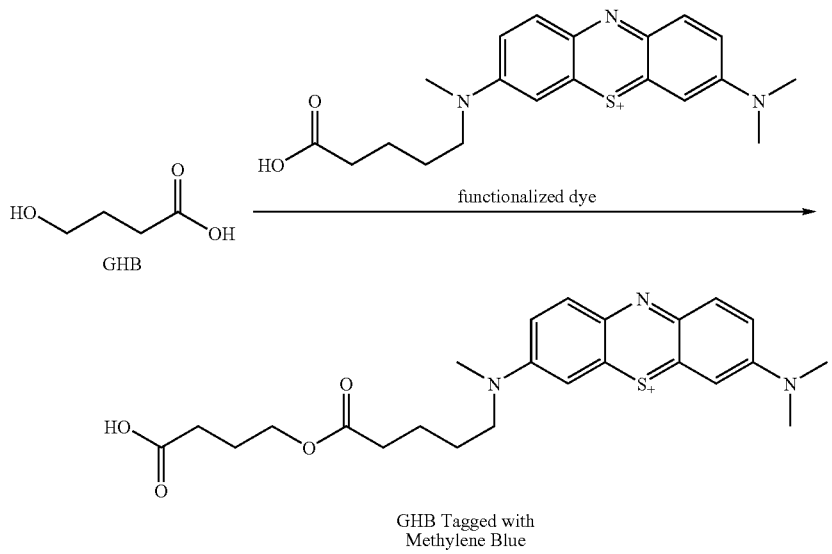

SCHEME V

GHB functionalized dye

GHB Tagged with Methylene Blue

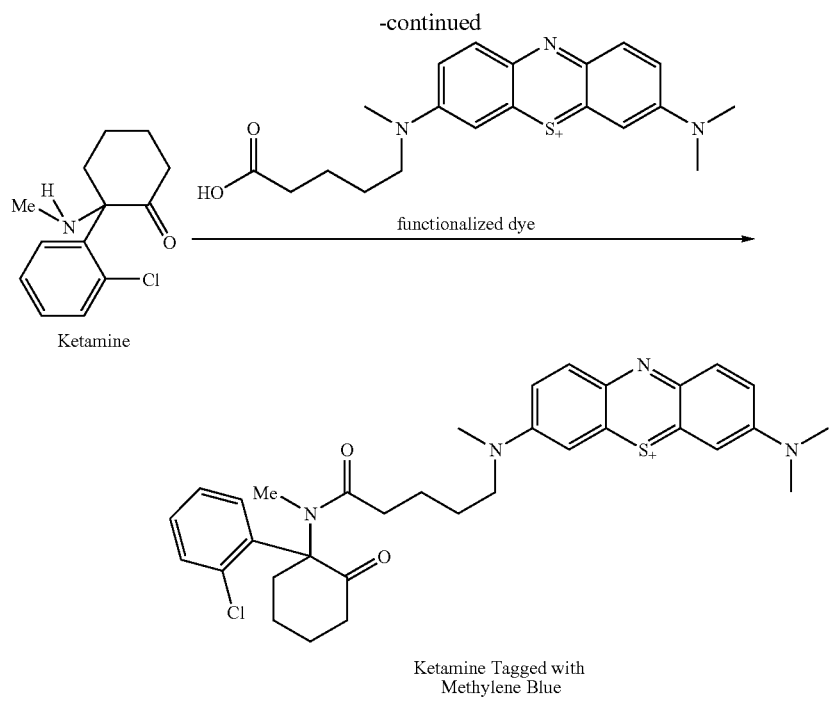

Ketamine Tagged with Methylene Blue

Generally, the displacement molecules are introduced into the molecularly imprinted crosslinked polymer by adding the polymer to a solution of the displacement molecule and allowing the displacement molecule to be absorbed into the binding sites of the swollen polymer. For example, for the cortisol-methylene blue displacement molecule, the polymer can be added to a solution of cortisol-methylene blue displacement molecule in methanol.

Figure 3A:
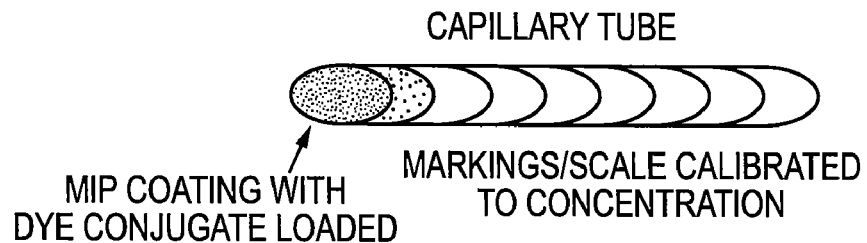
FIGS. 3A and 3B are schematic drawings of a sensor device according to one embodiment of the present invention.
Figure 3B:
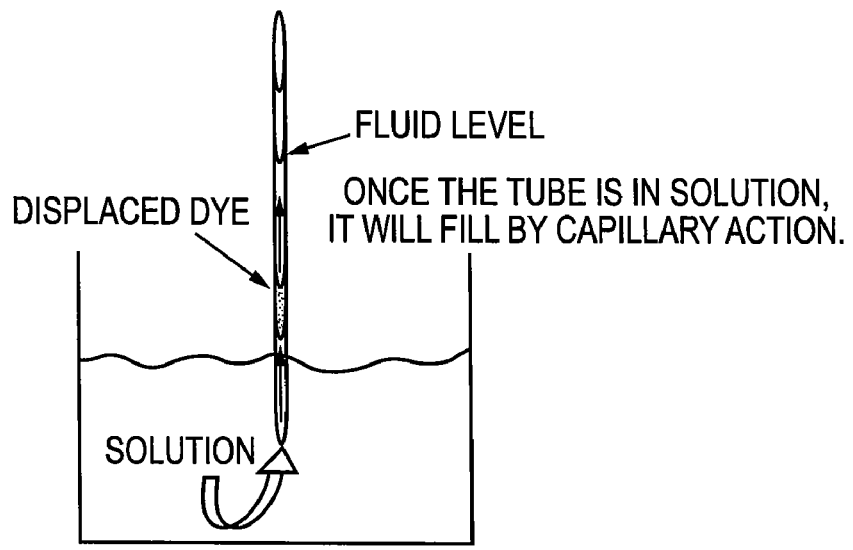

Next, the sensor devices of the present invention can be employed to determine whether the target molecule is in a fluid. For example, the molecularly imprinted crosslinked polymer can be coated onto the inside surface of a housing, e.g., a capillary tube, as generally depicted in FIG. 3A. As one skilled in art will readily appreciate, the arms of the molecularly imprinted crosslinked polymer may have to functionalized with a silanizing reagent so that they will bond to glass. Methods for bonding the silanized polymers to glass are within the purview of one skilled in the art, e.g., using alcohol and an acid or base catalyst. In use, the coated capillary tube would be of an appropriate inner dimension so as to draw fluid up the tube by capillary action. If the fluid of interest has the target molecule therein, the target molecule would displace the displacement molecules inside the molecularly imprinted crosslinked polymer coated at the end of the tube. This is because the exchange of target molecule and displacement molecule is more rapid than the flow of the fluid. As the displacement molecules are displaced from the molecularly imprinted crosslinked polymer, they will rise in the tube with the flow. See, e.g., FIG. 3B. The removal of color shows the target molecule was present in the fluid as the fluid will undergo a detectable color change. The detectable color change in the fluid is typically a visible change. The distance that the displacement molecule is removed up the tube is related to the concentration of target molecule in the fluid. Tubes can be loaded so as to have color change in a relevant analytical range. A scale will be provided to measure the length of displacement molecule clearance that is calibrated in amount of target molecule. The scale may be colored to improve color contrast. The tubes would be either disposable or recyclable.

In one embodiment, a capillary tube coated with the molecularly imprinted crosslinked polymer can be used to determine whether a drug such as a date rape drug is present in beverage. For example, a person can insert, for example, a capillary tube, into a beverage and if the date rape drug is in the beverage it will displace the displacement molecule containing the same date rape drug and colorimetric indicator. The calorimetric indicator will change the color of the fluid in the tube thereby indicating the presence of the drug.

The following examples are provided to enable one skilled in the art to practice the invention and are merely illustrative of the invention. The examples should not be read as limiting the scope of the invention as defined in the claims.

EXAMPLE 1

Step I: Preparation of 4-Nitrosodimethylaniline Hydrochloride

4-Nitrosodimethylaniline (4.0 g) was treated with 20 mL of 6M HCl solution. The green solid quickly changed to a lighter yellow-green color. After stirring for a few minutes, the solid clumps were broken up with a glass rod, and the yellow-green solid was filtered off. The product was washed with 6M HCl solution followed by methanol. The solid was dried under vacuum to give the hydrochloride salt (3.99 g, 80%).

Step II: Preparation of 2-amino-5-dimethylaniline Thiosulfuric Acid

4-Nitrosodimethylaniline hydrochloride (4.0 g, 21.4 mmol) of step I was added to a solution of glacial acetic acid (8 mL) in water (24 mL). The suspension was cooled to 0° C. in an ice bath and a solution of sodium thiosulfate pentahydrate (23.5 g, 94.1 mmol) in water (24 mL) was slowly added over 15 minutes. The solution darkened considerably during the addition. The reaction was stirred at 0° C. for four hours and then stirred at room temperature for 40 hours. A beige precipitate formed and the solution became transparent and pale green in color. The precipitate was filtered off and washed with a 1:9 acetic acid:water solution washing was continued with acetone until the filtrate was clear. The solid was dried under vacuum (2.32 g, 44%). Melting point values (203-204° C., decomp.).

EXAMPLE 2

Step I: Preparation of Ethyl 5-(N-methylanilato)valerate

A round-bottom flask was charged with N-methylaniline (2.60 mL, 23.9 mmol) and acetonitrile (40 mL). A syringe was used to add ethyl 5-bromovalerate (4.0 mL, 25.1 mmol) and 2,6-lutidine (2.91 mL, 25.1 mmol). The reaction was heated at reflux for 40 hours, at which point the solution was a pale green-brown color. Acetonitrile was removed under vacuum and residues were dissolved in ether and water. The organic phase was collected and washed with water. After drying over magnesium sulfate and filtering, the solvent was removed to give a brown liquid. The crude product was purified by column chromatography (10% ethyl acetate/hexanes) and was collected as a pale yellow liquid (4.96 g, 88%).

Step II: Preparation of 5-(N-methylanilato)valeric Acid Hydrochloride

Ethyl 5-(N-methylanilato)valerate (2.0 g, 8.50 mmol) of step I was dissolved in methanol (5 mL). A solution of sodium hydroxide (340 mg, 8.50 mmol) in water (5 mL) was added and the reaction was heated at reflux for three hours. After cooling, 1M HCl solution was slowly added until the pale yellow solution was acidic to pH paper. The solvents were then removed under vacuum and the residues were dissolved in acetonitrile. The precipitated sodium chloride was filtered off and the solvent was removed to give 5-(N-methylanilato) valeric acid hydrochloride as a clear oil (1.95 g, 97%).

EXAMPLE 3

Step I: Preparation of Carboxylic Acid-Functionalized Methylene Blue 5-(N-methylanilato)valeric acid hydrochloride (1.66 g, 6.81 mmol) of Example 2 and 2-amino-5-dimethylaniline thiosulfuric acid (1.61 g, 6.47 mmol) of Example 1 were combined in a round-bottom flask with 1M HCl solution (6 mL) and water (84 mL). The suspension was cooled to 0° C. in an ice bath and a solution of potassium dichromate (1.27 g, 4.32 mmol) dissolved in water (12 mL) was added dropwise by pipette over 15 minutes. The dark green reaction was stirred at 0° C. for one hour. Glacial acetic acid (180 mg) was added and the reaction was stirred for and additional hour at room temperature. The solution was filtered to give a purple-blue solid, which was washed with water. The solid was then dissolved in acetonitrile (80 mL) to give a purple-black suspension. Manganese(IV) oxide (1.58 g, 18.2 mmol) and a catalytic amount of copper(II) sulfate were added and the reaction was heated at reflux for 90 minutes. The color changed from dark green to deep blue. The reaction was filtered and washed thoroughly with acetonitrile and water. The filtrate was concentrated, loaded onto a silica gel column, and eluted with acetonitrile. A dark yellow band and a blue band were collected, then the solvent system was switched to 1:5:40 1M HCl:water:acetonitrile. A small blue band was collected followed by a major dark blue band containing the product, followed by a small blue band of side product. The dark blue band was dried under vacuum to give a blue-purple crystalline solid (650 mg, 28%).

Step II: Preparation of Methylene Blue-Labeled Cortisol

A round-bottom flask was charged with carboxylic acid-functionalized methylene blue (262 mg, 0.68 mmol) of step I, cortisol (746 mg, 2.05 mmol), 4-dimethylaminopyridine (42 mg, 0.34 mmol) and dry dimethylformamide (DMF) (10 mL). The dark blue solution was cooled to 0° C. and 1,3-dicyclohexylcarbodiimide (212 mg, 1.02 mmol) was added. The reaction was warmed to room temperature and stirred for five days. Ethyl acetate was added and the blue solution was filtered. The purple solids were washed with ethyl acetate until the filtrate was clear. The filtrate was directly loaded (not concentrated) onto a silica gel column and eluted with ethyl acetate until all the organics (unreacted cortisol) had eluted (monitored by TLC). All the blue material remained at the top of the column. The eluant was changed to 1:5:40 1M HCl: water:acetonitrile and blue bands began to elute. A light blue band was followed by a major dark blue band containing the product. The solvent was removed to give a blue solid, which was dissolved in acetonitrile and filtered to remove silica gel that had dissolved during the purification column. Solvent removal gave the product as a blue-purple waxy solid (30 mg, 6%).

EXAMPLE 4

Preparation of Trimethylolpropane Triacrylate (TMPTA) RAFT Agent

Trimethylolpropane triacrylate was purified by passing it trough a pipette packed with hydroquinone inhibitor remover (Sigma-Aldrich cat. no. 311332) and then through a pipette filled with activated alumina. TMPTA (2.03 g, 6.8 mmol) and an excess of freshly prepared dithiobenzoic acid (6.97 g, 45.3 mmol) were dissolved in 40 mL of methylene chloride. The pink solution was allowed to reflux for 6 hours. The solution was cooled to room temperature and the solvent was evaporated off under vacuum. The dark red crude material was dry mounted on a silica column and eluted with a 10% ether: hexanes solution. A purple band and then a pink band were eluted. After all the pink compound was removed, the product began to elute as an orange band. The mobile phase was changed to 50% ether:hexanes and the product was collected. The solvent was removed under vacuum to give the product as a viscous red oil. This material was stored in the freezer at 0° C.

EXAMPLE 5

Preparation of Hex-5-enyl Methacrylate

5-Hexen-1-ol (5.0 g; 50.0 mmol) and triethylamine (15.0 g, 150 mmol) were combined in a round-bottom flask and dissolved in methylene chloride (50 mL). After cooling in an ice bath, methacryloyl chloride (5.2 g, 50.0 mmol) was slowly added to the solution by syringe. The solution was warmed to room temperature and allowed to stir overnight. Water was added, and the organic phase was washed with sodium bicarbonate solution followed by brine solution. The organic layer was dried over magnesium sulfate and filtered to give a clear solution. After solvent removal, the crude product was purified by passing it through a silica column (1:40 ethyl acetate: hexanes). The product was obtained as a clear liquid, which was stored at 0° C.

EXAMPLE 6

Preparation of Crosslinkable Poly(Methyl Methacrylate) Star Polymer

Methyl methacrylate monomer was stripped of radical inhibitors by passage through a pipette packed with neutral alumina followed by a pipette pack with inhibitor remover (Aldrich). A Schlenk tube was charged with methyl methacrylate (1.0 mL, 9.34 mmol), hex-5-enyl methacrylate (393 mg, 2.33 mmol), trimethylolpropane triacrylate RAFT agent (44 mg, 58.4 µmol), and AIBN initiator (2.0 mg, (12.1 µmol). Anhydrous toluene (1.0 mL) was added to give a light pink solution. The reaction was sealed and degassed via sequential freeze-pump-thaw cycles before being placed under nitrogen and immersed in an oil bath at 40° C. The temperature was ramped from 40° C. to 70° C. over a period of fifty minutes. After stirring for a total of 16 hours, the viscous solution was precipitated in hexanes, filtered and dried under vacuum to give a light pink solid (415 mg). NMR analysis indicated that the star polymer contains 25 mol % crosslinker content.

EXAMPLE 7

Crosslinking/Imprinting the Star Polymer with Cortisol

A three-neck flask equipped with a reflux condenser was charged with crosslinkable star poly(methyl methacrylate) (150 mg) of Example 6, Grubbs second-generation olefin metathesis catalyst (benzylidene[1,3-bis(2,4,6-trimethylphenyl)-2-imidazolidinylidene]dichloro(tricyclohexylphosphine)ruthenium, 10 mg), and an excess of cortisol (150 mg). The flask was placed under nitrogen and dry THF (75 mL) was added via cannula. The pink solution was heated at reflux under nitrogen for six hours. The color changed to clear brown. The solvent was concentrated under vacuum, and then the polymer and excess cortisol were precipitated in hexanes. Solids were collected by filtration and then washed thoroughly with methanol to remove excess cortisol. The light brown polymer product was redissolved in a few milliliters of methylene chloride and passed through an alumina column to remove ruthenium byproducts. Precipitation in hexanes yielded a white polymer (110 mg). UV analysis of the polymer indicated that cortisol was still present, consistent with the formation of crosslinked binding sites in the polymer. The cortisol was removed by Soxhlet extraction with methanol until the cortisol absorption at 230 nm was no longer detectable.

EXAMPLE 8

MIP Loading with Dye Conjugate

Methylene blue tagged cortisol (1.0 mg) was dissolved in methanol (10 mL) to give a deep blue solution. The crosslinked, cortisol-imprinted poly(methyl methacrylate) star polymer (20 mg) of Example 7 was added to the methanol solution. The mixture was stirred vigorously overnight, at which point the polymer was noticeably blue in color. The dye-loaded polymer was collected by filtration and washed with cold methanol (10 mL). The polymer was then re-suspended in methanol and stirred overnight in order to remove dye molecules that were attached to the polymer through non-specific binding interactions. The dye-loaded polymer was filtered and dried under vacuum to give the loaded MIP as a medium blue solid.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A molecularly imprinted polymer sensor device for detecting the presence of a taggant molecular structure in a fluid, comprising:
   a molecularly imprinted crosslinked polymer having a crosslinked core and a plurality of polymer arms attached to the core, wherein
   the core has molecular sized cavities adapted to selectively receive and bind displacement molecules having the taggant molecular structure and a colorimetric indicator,
   said displacement molecule is selectively removed from the molecularly imprinted crosslinked polymer and replaced with the taggant molecular structure upon exposure to the fluid containing the taggant molecular structure therein, thereby indicating the presence of the taggant molecular structure in the fluid based on a loss of color along the length of a housing, and
   said polymer is imprinted prior to having the colorimetric indicator added.

2. The sensor device of claim 1, wherein the taggant molecular structure is selected from the group consisting of a hormone, drug or drug residue.

3. The sensor device of claim 2, wherein the hormone is cortisol.

4. The sensor device of claim 3, wherein the fluid is a biological fluid.

5. The sensor device of claim 4, wherein the biological fluid is saliva or blood.

6. The sensor device of claim 2, wherein the drug is selected from the group consisting of gamma hydroxybutyric acid, flunitrazepam, ketamine, gamma-hydroxybutyrate (GHB), gamma butyrolactone (GBL) and mixtures thereof.

7. The sensor device of claim 6, wherein the fluid is a beverage.

8. The sensor device of claim 1, wherein the housing comprises an inlet for receiving the fluid, the inlet having a coating on at least a portion of the inside of the surface thereof, the coating comprising the molecularly imprinted crosslinked polymer.

9. The sensor device of claim 8, wherein the housing is a capillary tube.

10. The sensor device of claim 3, wherein the colorimetric indicator is methylene blue.

11. The sensor device of claim 6, wherein the colorimetric indicator is methylene blue.

12. The sensor device of claim 1, wherein the molecularly imprinted crosslinked polymer is prepared by (a) reacting at least one functional monomer and a Reversible Addition Fragmentation Chain Transfer (RAFT) agent in the presence of an initiator; (b) crosslinking the product of step (a) with a crosslinking agent and the taggant molecular structure in the presence of a Grubb catalyst under olefin metathesis reaction conditions to form a molecularly imprinted crosslinked polymer containing the taggant molecular structure; (c) removing the taggant molecular structure from the molecularly imprinted crosslinked polymer; and (d) incorporating the displacement molecules into the molecularly imprinted crosslinked polymer.

* * * * *